(12) United States Patent  
Ueda et al.

(10) Patent No.: US 6,998,132 B1
(45) Date of Patent: Feb. 14, 2006

(54) ENVELOPED PESTICIDAL FORMULATIONS

(75) Inventors: Nobuhito Ueda, Ashiya (JP); Toshiro Ohtsubo, Sanda (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/485,820

(22) PCT Filed: Jun. 14, 1999

(86) PCT No.: PCT/JP99/03166

§ 371 (c)(1),
(2), (4) Date: Feb. 16, 2000

(87) PCT Pub. No.: WO99/65302

PCT Pub. Date: Dec. 23, 1999

(30) Foreign Application Priority Data

Jun. 17, 1998  (JP) ................................. 10-169917
Dec. 24, 1998  (JP) ................................. 10-367061

(51) Int. Cl.
 *A01N 25/14* (2006.01)

(52) U.S. Cl. ...................... 424/409; 424/405; 424/406; 424/408; 424/417; 424/418; 424/419; 424/420; 424/421; 504/100; 504/101

(58) Field of Classification Search ................ 424/405, 424/406, 408, 409, 411, 417–421; 504/100, 504/101
See application file for complete search history.

(56) References Cited

U.S. PATENT DOCUMENTS

| 3,607,812 | A | * | 9/1971 | Takigawa et al. ...... 260/29.6 B |
| 4,544,693 | A | * | 10/1985 | Surgant ...................... 524/375 |
| 5,639,465 | A | * | 6/1997 | Huang et al. ................ 424/409 |
| 5,698,210 | A | * | 12/1997 | Levy ........................... 424/406 |
| 5,929,053 | A | * | 7/1999 | Murakami et al. ............ 514/89 |
| 6,001,382 | A | * | 12/1999 | Levy ........................... 424/405 |

FOREIGN PATENT DOCUMENTS

| EP | 000579951 A1 | * | 1/1994 |
| JP | 05 017308 A | | 1/1993 |
| JP | 5-78204 | | 3/1993 |
| JP | 5-78207 | | 3/1993 |
| JP | 05 085901 A | | 4/1993 |
| JP | 06 80186 A | | 3/1994 |
| JP | 6-321704 | | 11/1994 |
| JP | 08 119803 A | | 5/1996 |
| WO | 9201378 | * | 2/1992 |
| WO | WO 92/01378 A | | 2/1993 |
| WO | WO 96/03871 A | | 2/1996 |
| WO | WO 97/03558 | | 2/1997 |

* cited by examiner

*Primary Examiner*—Neil S. Levy
(74) *Attorney, Agent, or Firm*—Sughrue Mion, PLLC

(57) ABSTRACT

A solid pesticidal formulation, such as wettable powders, water dispersible granules and water soluble formulations, enveloped in a water soluble substance, such as polyvinyl alcohol and so on, wherein the solid pesticidal formulation comprises at least one water soluble hydroxy compound selected from the group consisting of alkanols, alkylene glycols, glycol monoethers, tri- or more valent alcohols, alcoholamines, hydroxyfatty acids and hydroxyfatty acid esters, or water soluble glycol ether acetates is excellent in stability after preserved.

3 Claims, No Drawings

ENVELOPED PESTICIDAL FORMULATIONS

TECHNICAL FIELD

The present invention relates to an enveloped pesticidal formulations.

BACKGROUND ART

In pesticidal formulations, wettable powders, water dispersible granules, water soluble formulations and the like are solid formulations, but they are applied to the objected plants, cultivated soil and the like as their diluted solution after diluted with water. The solid formulations enveloped in water soluble polymer film or water soluble paper, which can be applied into water to give a dilution as they are, are described for the purpose of preventing a drift of the solid formulations and further saving labor when preparing the dilution (cf. JP-sho60-61504A, JP-sho60-45180A, etc.).

However, these enveloped pesticidal formulations are not sufficiently stable. It was troublesome that the envelope material may degenerate while they are preserved for a long time and may be broken while preserved or transported, and further a sprayer may be blocked in case of applying the dilution to plants.

DISCLOSURE OF THE INVENTION

In the solid pesticidal formulations such as wettable powders, water dispersible granules and water soluble formulations enveloped in a water soluble substance, the present invention provides an excellent enveloped pesticidal formulation that is characteristic of stability even after preserved for a long time. Said enveloped pesticidal formulation has a specific water soluble compound in a solid pesticidal formulation and can solve the former problems.

The present invention is a solid pesticidal formulation enveloped in a water soluble substance wherein the solid pesticidal formulation comprises at least one water soluble hydroxy compound selected from the group consisting of alkanols, alkylene glycols, glycol monoethers, tri- or more valent alcohols, alcoholamines, hydroxyfatty acids and hydroxyfatty acid esters. Further, the present invention is also a solid pesticidal formulation enveloped in a water soluble substance wherein the solid pesticidal formulation comprises a water soluble glycol ether acetate.

The water soluble hydroxy compounds and the water soluble glycol ether acetates utilized in the present invention usually have one or more of water solubility, namely the number of grams of the water soluble hydroxy compound or the water soluble glycol ether acetate dissolvable in 100 g of water, at ordinary temperature. In the water soluble hydroxy compounds, liquid hydroxy compounds at ordinary temperature are preferable since it is possible to add the hydroxy compounds homogeneously. Typical examples include isobutyl alcohol, ethylene glycol, propylene glycol, butylene glycol, ethylene glycol monomethyl ether, diethylene glycol monomethyl ether, glycerin, monoethanolamine, diethanolamine, triethanolamine, lactic acid and ethyl lactate. In these examples, glycerin and ethylene glycol are preferable, and especially, glycerin is more preferable. Furthermore, in the water soluble glycol ether acetates, liquid compounds at ordinary temperature are also preferable since it is possible to add the compounds homogeneously. Typical examples include ethylene glycol monomethyl ether acetate and ethylene glycol monoethyl ether acetate.

In the present invention, the amount of the water soluble hydroxy compound in the solid pesticidal formulation is usually 0.1 to 40% by weight, preferably 2 to 20% by weight. And the amount of the water soluble glycol ether acetate in the solid pesticidal formulation is usually 0.1 to 40% by weight, preferably 2 to 20% by weight.

The pesticidal active ingredients in the solid pesticidal formulation are illustrated by the active ingredient compounds of insecticides, fungicides, herbicides, plant growth regulators, insect growth regulators and so on, and the examples are shown as follows:

organophosphorus compounds such as fenitrothion [O,O-dimethyl O-(3-methyl-4-nitrophenyl) phosphorothioate], fenthion [O,O-dimethyl O-(3-methyl-4-(methylthio)phenyl) phosphorothioate], diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], acephate [O,S-dimethyl acetylphosphoramidothioate], methidathion [S-2,3-dihydro-5-methoxy-2-oxo-1,3,4-thiadiazol-3-ylmethyl O,O-dimethyl phosphorodithioate], disulfoton [O,O-diethyl S-2-ethylthioethyl phosphorodithioate], DDVP [2,2-dichlorovinyl dimethyl phosphate], sulprofos [O-ethyl O-4-(methylthio) phenyl S-propyl phosphorodithioate], cyanofos [O-4-cyanophenyl O,O-dimethyl phosphorothioate], dioxabenzofos [2-methoxy-4H-1,3,2-benzodioxaphosphorin-2-sulfide], dimethoate [O,O-dimethyl S-(N-methylcarbamoylmethyl)dithiophosphate], phenthoate [ethyl 2-dimethoxyphosphinothioylthio(phenyl)acetate], malathion [diethyl (dimethoxyphosphinothioylthio)succinate], trichlorfon [dimethyl 2,2,2-trichloro-1-hydroxyethylphosphonate], azinphos-methyl [S-3,4-dihydro-4-oxo-1,2,3-benzotriazin-3-ylmethyl O,O-dimethyl phosphorodithioate], monocrotophos [dimethyl {(E)-1-methyl-2-(carbamoyl)vinyl}phosphate], ethion [O,O,O', O'-tetraethyl-S,S'-methylenebis(phosphorodithioate)], and the like; carbamate compounds such as BPMC [2-sec-butylphenyl methylcarbamate], benfuracarb [ethyl N-{2, 3-dihydro-2,2-dimethylbenzofuran-7-yloxycarbonyl(methyl)aminothio}-N-isopropyl-β-alaninate], propoxur [2-isopropylphenyl N-methylcarbamate], carbosulfan [2,3-dihydro-2,2-dimethyl-7-benzo[b]furanyl N-dibutylaminothio-N-methylcarbamate], carbaryl [1-naphthyl N-methylcarbamate], methomyl [S-methyl N-(methylcarbamoyloxy)thioacetimidate], ethiofencarb [2-(ethylthiomethyl)phenyl methylcarbamate], aldicarb [2-methyl-2-(methylthio)propionaldehyde O-methylcarbamoyloxime], oxamyl [N,N-dimethyl-2-methylcarbamoyloxyimino-2-(methylthio)acetamide], fenothiocarb [S-4-phenoxybutyl N,N,-dimethylthiocarbamate], and the like; pyrethroid compounds such as etofenprox [2-(4-ethoxyphenyl)-2-methyl-1-(3-phenoxybenzyl)oxypropane], fenvalerate [(RS)-α-cyano-3-phenoxybenzyl (RS)-2-(4-chlorophenyl)-3-methylbutyrate], esfenvalerate [(S)-α-cyano-3-phenoxybenzyl (S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS)-cis,trans-3-(2,2-dichlorovinyl)-2, 2-dimethylcyclopropanecarboxylate], permethlin [3-phenoxybenzyl (1RS)-cis,trans-3-(2,2-dichlorovinyl)-2,2-dimethylcyclopropanecarboxylate], cyhalothrin [(RS)-α-cyano-3-phenoxybenzyl (1RS,3Z)-cis-3-(2-chloro-3,3,3-trifluoroprop-1-enyl)-2,2-dimethylcyclopropanecarboxylate], deltamethrin [(S)-α-cyano-3-phenoxybenzyl (1R)-cis-3-(2,2-dibromovinyl)-2,2-dimethylcyclopropanecarboxylate], cycloprothrin [(RS)-

α-cyano-3-phenoxybenzyl (RS)-2,2-dichloro-1-(4-ethoxyphenyl) cyclopropanecarboxylate], fluvalinate [α-cyano-3-phenoxybenzyl N-(2-chloro-α, α, α-trifluoro-p-tolyl)-D-valinate], biphenthrin [2-methyl-3-phenybenzyl (1RS,3Z)-cis-3-(2-chloro-3,3,3-trifluoro-1-propenyl)-2,2-dimethylcyclopropanecarboxylate], halfenprox [2-(4-bromodifluoromethoxyphenyl)-2-methyl-1-(3-phenoxybenzyl) methylpropane], tralomethrin [(S)-α-cyano-3-phenoxybenzyl (1R)-cis-3-(1,2,2,2-tetrabromoethyl)-2,2-dimethylcyclopropanecarboxylate], silafluofen [(4-ethoxyphenyl)-{3-(4-fluoro-3-phenoxyphenyl)propyl}dimethylsilane], d-phenothrin [3-phenoxybenzyl (1R)-cis,trans-2,2-dimethyl-3-(2-methyl-1-propenyl)cyclopropanecarboxylate], cyphenothrin [(RS)-α-cyano-3-phenoxybenzyl (1R)-cis,trans-2,2-dimethyl-3-(2-methyl-1-propenyl)cyclopropanecarboxylate], d-resmethrin [5-benzyl-3-furylmethyl (1R)-cis,trans-2,2-dimethyl-3-(2-methyl-1-propenyl) cyclopropanecarboxylate], acrinathrin [(S)-α-cyano-3-phenoxybenzyl (1R,3Z)-cis-(2,2-dimethyl-{3-oxo-3-(1,1,1,3,3,3-hexafluoropropyloxy) propenyl}cyclopropanecarboxylate], cyfluthrin [(RS)-α-cyano-4-fluoro-3-phenoxybenzyl 3-(2,2-dichlorovinyl)-2,2-dimethylcyclopropanecarboxylate], tefluthrin [2,3,5,6-tetrafluoro-4-methylbenzyl (1RS,3Z)-cis-3-(2-chloro-3,3,3-trifluoro-1-propenyl)-2,2-dimethylcyclopropanecarboxylate], transfluthrin [2,3,5,6-tetrafluorobenzyl (1R)-trans-3-(2,2-dichlorovinyl)-2,2-dimethylcyclopropanecarboxylate], tetramethrin [3,4,5,6-tetrahydrophthalimidomethyl (1RS)-cis,trans-2,2-dimethyl-3-(2-methyl-1-propenyl) cyclopropanecarboxylate], allethrin [(RS)-2-methyl-4-oxo-3-(2 -propenyl)-2-cyclopenten-1-yl (1RS)-cis,trans-2,2-dimethyl-3-(2-methyl-1-propenyl) cyclopropanecarboxylate], prallethrin [(S)-2-methyl-4-oxo-3-(2-propynyl)-2-cyclopenten-1-yl (1R)-cis,trans-2,2-dimethyl-3-(2-methyl-1-propenyl) cyclopropanecarboxylate], empenthrin [(RS)-1-ethynyl-2-methyl-2-pentenyl (1R)-cis,trans-2,2-dimethyl-3-(2-methyl-1-propenyl) cyclopropanecarboxylate], imiprothrin [2,5-dioxo-3-(2-propynyl) imidazolidin-1-yl-methyl (1R)-cis,trans-2,2-dimethyl-3-(2-methyl-1-propenyl)cyclopropanecarboxylate], d-furamethrin [5-(2-propynyl) furufuryl (1R)-cis,trans-2,2-dimethyl-3-(2-methyl-1-propenyl) cyclopropanecarboxylate], 5-(2-propynyl) furufuryl 2,2,3,3-tetramethylcyclopropanecarboxylate, and the like; thiadiazine derivatives such as buprofezin [2-tert-butylimino-3-isopropyl-5-phenyl-1,3,5-thiadiazin-4-one] and the like; nitroimidazolidine derivatives; nereistoxin derivatives such as cartap [S,S'-(2-dimethylaminotrimethylene)bis (thiocarbamate)], thiocyclam [N,N-dimethyl-1,2,3-trithian-5-ylamine], bensultap [S,S'-2-dimethylaminotrimethylenedi(benzenethiosulfonate)], and the like; N-cyanoamidine derivatives such as N-cyano-N'-methyl-N'-(6-chloro-3-pyridylmethyl)acetamidine and the like; chlorinated hydrocarbon compounds such as endosulfan [6,7,8,9,10,10-hexachloro-1,5,5a,6,9,9a-hexahydro-6,9-methano-2,4,3-benzodioxathiepine oxide], γ-BHC [1,2,3,4,5,6-hexachlorocyclohexane], dicofol [1,1-bis(4-chlorophenyl)-2,2,2-trichloroethanol], and the like; benzoylphenylurea compounds such as chlorfluazuron [1-{3,5-dichloro-4-(3-chloro-5-trifluoromethylpyridin-2-yloxy)phenyl}-3-(2,6-difluorobenzoyl)urea], teflubenzuron [1-(3,5-dichloro-2,4-difluorophenyl)-3-(2,6-difluorobenzoyl)urea], flufenoxuron [1-{4-(2-chloro-4-trifluoromethylphenoxy)-2-fluorophenyl}-3-(2,6-difluorobenzoyl) urea], and the like; formamidine derivatives such as amitraz [N,N' -{(methylimino)dimethylidine}-di-2,4-xylidine], chlordimeform [N'-(4-chloro-2-methylphenyl)-N,N-dimethylmethynimidamide], and the like; thiourea derivatives such as diafenthiuron [N-(2,6-diisopropyl-4-phenoxyphenyl)-N'-t-butylcarbodiimide] and the like; N-phenylpyrazole compounds; metoxadiazone [5-methoxy-3-(2-methoxyphenyl)-1,3,4-oxadiazol-2 (3H)-one]; bromopropylate [isopropyl 4,4'-dibromobenzilate]; tetradifon [4-chlorophenyl 2,4,5-trichlorophenyl sulfone]; chinomethionat [S,S-6-methylquinoxaline-2,3-diyl dithiocarbonate]; propargite [2-(4-tert-butylphenoxy) cyclohexylprop-2-ynyl sulfite]; fenbutatin oxide [bis{tris (2-methyl-2-phenylpropyl)tin}oxide]; hexythiazox [(4RS,5RS)-5-(4-chlorophenyl)-N-chlorohexyl-4-methyl-2-oxo-1,3-thiazolidine-3-carboxamide]; clofentezine [3,6-bis(2-chlorophenyl)-1,2,4,5-tetrazine]; pyridaben [2-tert-butyl-5-(4-tert-butylbenzylthio)-4-chloropyridazin-3(2H)-one]; fenpyroximate [tert-butyl (E)-4-[(1, 3-dimethyl-5-phenoxypyrazol-4-yl)methyleneaminooxymethyl]benzoate]; tebufenpyrad [N-(4-tert-butylbenzyl)-4-chloro-3-ethyl-1-methyl-5-pyrazolecarboxamide]; polynactin complex [tetranactin, dinactin, trinactin], pyrimidifen [5-chloro-N-[2-{4-(2-ethoxyethyl)-2,3-dimethylphenoxy}ethyl]-6-ethylpyrimidin-4-amine]; milbemectin; abamectin; ivermectin; azadirachtin [AZAD]; 5-methyl[1,2,4]triazolo[3,4-b] benzothiazole; methyl 1-(butylcarbamoyl)benzimidazol-2-carbamate; 6-(3,5-dichloro-4-methylphenyl)-3 (2H)-pyridazinone; 1-(4-chlorophenoxy)-3,3-dimethyl-1-(1H-1,2,4-triazol-1-yl)butanone; (E)-4-chloro-2-(trifluoromethyl)-N-[1-(imidazol-1-yl)-2-propoxyethylidene]aniline; 1-[N-propyl-N-[2-(2,4,6-trichlorophenoxy)ethyl]carbamoyl]imidazole; (E)-1-(4-chlorophenyl)-4,4-dimethyl-2-(1H-1,2,4-triazol-1-yl)-1-penten-3-ol; 1-(4-chlorophenyl)-4,4-dimethyl-2-(1H-1,2,4-triazol-1-yl)-pentan-3-ol; (E)-1-(2,4-dichlorophenyl)-4,4-dimethyl-2-(1H-1,2,4-triazol-1-yl)-1-penten-3-ol; 1-(2,4-dichlorophenyl)-4,4-dimethyl-2-(1H-1,2,4-triazol-1-yl)pentan-3-ol; 4-[3-(4-tert-butylphenyl)-2-methylpropyl]-2,6-dimethylmorpholine; 2-(2,4-dichlorophenyl)-1-(1H-1,2,4-triazol-1-yl)hexan-2-ol; O,O-diethyl O-2-quinoxalinyl phosphorothioate; O-(6-ethoxy-2-ethyl-4-pyrimidinyl) O,O-dimethyl phosphorothioate; 2-diethylamino-5,6-dimethylpyrimidin-4-yl dimethylcarbamate; 4-(2,4-dichlorobenzoyl)-1,3-dimethyl-5-pyrazolyl p-toluenesulfonate; 4-amino-6-(1,1-dimethylethyl)-3-methylthio-1,2,4-triazin-5 (4H)-one; 2-chloro-N-[(4-methoxy-6-methyl-1,3,5-triazin-2-yl)aminocarbonyl] benzenesulfonamide; 2-methoxycarbonyl-N-[(4,6-dimethoxypyrimidin-2-yl)aminocarbonyl] benzenesulfonamide; 2-methoxycarbonyl-N-[(4,6-dimethylpyrimidin-2-yl)aminocarbonyl] benzenesulfonamide; 2-methoxycarbonyl-N-[(4-methoxy-6-methyl-1,3,5-triazin-2-yl)aminocarbonyl] benzenesulfonamide; 2-ethoxycarbonyl-N-[(4-chloro-6-methoxypyrimidin-2-yl)aminocarbonyl] benzenesulfonamide; 2-(2-chloroethoxy)-N-[(4-methoxy-6-methyl-1,3,5-triazin-2-yl)aminocarbonyl] benzenesulfonamide; 2-methoxycarbonyl-N-[(4,6-dimethoxypyrimidin-2-yl)aminocarbonyl] phenylmethanesulfonamide; 2-methoxycarbonyl-N-[(4-methoxy-6-methyl-1,3,5-triazin-2-yl)aminocarbonyl] thiophene-3-sulfonamide; 4-ethoxycarbonyl-N-[(4,6-dimethoxypyrimidin-2-yl)aminocarbonyl]-1-methylpyrazole-5-sulfonamide; 2-[4,5-dihydro-4-methyl-4-(1-methylethyl)-5-oxo-1H-imidazol-2-yl]-3-quinolinecarboxylic acid; 2-[4,5-dihydro-4-methyl-4-(1- methylethyl)-5-oxo-1H-imidazol-2-yl]-5-ethyl-3-pyridinecarboxylic acid; methyl 6-(4-isopropyl-4-methyl-5-oxoimidazolin-2-yl)-m-toluate; methyl 2-(4-isopropyl-4-methyl-5-oxoimidazolin-2-yl)-p-toluate; 2-(4-isopropyl-4-methyl-5-oxoimidazolin-2 -yl)nicotinic acid; N-(4-chlorophenyl)methyl-N-cyclopentyl-N'-phenylurea; and so on.

In the present invention, examples of the solid pesticidal formulations enveloped in the water soluble substance include water dispersible or soluble formulations such as wettable powders, water dispersible granules and water soluble formulations.

Each of wettable powders, water dispersible granules and water soluble formulations is utilized after diluted with water. When diluted with water, wettable powders and water dispersible granules usually give a dispersion and water soluble formulations usually give a solution. Water dispersible granules may be mentioned as dry flowables.

Wettable powders utilized in the present invention contain 0.5 to 90% by weight of pesticidal active ingredient, preferably 5 to 80% by weight, more preferably 25 to 50% by weight, and 0.1 to 50% by weight of surfactant that is a wetting agent or a dispersant, preferably 1 to 20% by weight, as well as the water soluble hydroxy compound. The wettable powders may optionally contain an antifoaming agent, a solvent, an inert carrier and so on.

Examples of the wetting agent in the wettable powders include polyoxyethylenealkyl phenyl ethers, sodium alkylbenzenesulfonates, dioctyl sulfosuccinate, sodium alkylnaphthalenesulfonates and sodium alkylsulfates, and examples of the dispersant include condensed formalin with naphthalenesulfonic acid salts, and sodium ligninsulfonate. Examples of the inert carrier in the wettable powders include clay, calcium carbonate, talc, diatomaceous earth, amorphous silicon dioxide and white carbon.

Water dispersible granules utilized in the present invention contain 0.5 to 90% by weight of pesticidal active ingredient, preferably 5 to 80% by weight, and 0.1 to 50% by weight of surfactant that is a wetting agent or a dispersant, preferably 1 to 20% by weight, as well as the water soluble hydroxy compound. The water dispersible granules may optionally contain a binder, an antifoaming agent, a disintegrant, a solvent, an inert carrier and so on.

Examples of the wetting agent in the water dispersible granules include sodium alkylnaphthalenesulfonates, sodium alkylsulfates, sodium alkylbenzenesulfonates, sodium alkylsulfosuccinates and polyoxyethylenealkyl aryl ethers, and examples of the dispersant include condensed formalin with alkylnaphthalenesulfonic acid salts, ligninsulfonic acid salts, polyacrylic acid salts, alkylarylsulfonic acid salts, polycarboxylic acid salts, polyoxyethylene polyoxypropylene block polymers, and polystyrene polyoxyethylene block polymers. Examples of the binders in the water dispersible granules include carboxymethylcellulose, polyvinyl alcohol, polyvinylpyrrolidone, dextrin and water soluble starch, and examples of the inert carrier include clay, calcium carbonate, bentonite, diatomaceous earth, glucose, lactose, sucrose, ammonium sulfate, sodium sulfate, urea, white carbon and amorphous silicon dioxide.

For the inert carrier utilized in the wettable powders or water dispersible granules, absorbents such as white carbon are preferable when the pesticidal active ingredient is liquid. And grinding additives such as amorphous silicon dioxide are preferable when the pesticidal active ingredient is solid.

Water soluble formulations utilized in the present invention contain 0.5 to 95% by weight of pesticidal active ingredient, as well as the water soluble hydroxy compound or water soluble glycol ether acetate. The water soluble formulations may optionally contain a wetting agent, an inert carrier and so on.

Examples of the wetting agent in the water soluble formulations include polyoxyethylenealkyl phenyl ethers, sodium alkylbenzenesulfonates, dioctyl sulfosuccinate, sodium alkylnaphthalenesulfonates and sodium alkylsulfates, and examples of the inert carrier include water soluble carriers such as glucose, lactose, sucrose, ammonium sulfate, sodium sulfate, urea and so on.

Water soluble formulations are powders or granules of solid formulation, and the active ingredient and the other components are soluble in water when diluted. In case that the active ingredient is water soluble and is not easy to be dissolved in organic solvents and that the active ingredient is appreciably hydrolyzed in water, water soluble formulations are preferably utilized. Powdery water soluble formulations may be mentioned as water soluble powders.

Solid pesticidal formulations can be prepared by usual methods.

Wettable powders are, for example, prepared by mixing and pulverizing each component. When a pesticidal active ingredient is solid, it is preferable to pulverize the pesticidal active ingredient prior to mixing. The pulverizing procedure is carried out for the pesticidal active ingredient solely or the pesticidal active ingredient with a grinding additive.

Examples of the pulverizer utilized for pulverizing the mixed components or preliminary pulverizing include jet mill and impact mill. Jet mill is well utilized for finely pulverizing the solid pesticidal active ingredient to $\mu$m order or less.

Water dispersible granules are usually prepared by mixing each component and granulating. The granulating methods are exemplified by fluidized-bed granulating, spray-dry granulating, extrusion granulating and pan granulating method. Suitable methods can be adopted by formulation types or physical properties.

Fluidized-bed granulating is a method that is spraying a solution or dispersion containing a binder to fluid powders, aggregating the powders, granulating and drying them. Spray-dry granulating is a method that is spraying a solution or suspension into hot air for drying to give granules. Extrusion granulating is a method that is adding water and a binder to powders, kneading them, extruding them from the holes of screen and drying to give granules. Pan granulating is a method that is providing powders into a rotating pan or drum and adding water while rotating to give granules, and is suitable for round granules.

Further, pesticidal active ingredients can be pulverized prior to mixing with the other components as well as the preparation of wettable powders when the pesticidal active ingredient is solid.

Water soluble formulations are prepared by mixing each component. Pesticidal active ingredients can be pulverized prior to mixing with the other components as well as the preparation of wettable powders when the pesticidal active ingredient is solid. Furthermore, water soluble powders can be granulated by the same methods as the water dispersible granules mentioned above.

Moreover, the other formulation method is provided by preparing solid formulation without water soluble hydroxy compounds or water soluble glycol ether acetate and then impregnating a water soluble hydroxy compound or glycol ether acetate, or their solution into the solid formulation and drying if necessarily.

Examples of the water soluble substance utilized for the envelop include water soluble polymers such as polyvinyl alcohol, hydroxypropylcellulose, hydroxypropylmethylcellulose, methylcellulose, sodium polyacrylate, alkali metal salts of alginic acid such as sodium salt, gelatin, pullulan, water soluble starch, sodium carboxymethylcellulose, polyethyleneglycol and the like. Especially, water soluble polymer comprising polyvinyl alcohol is preferable because of good solubility even in cold water. Enveloping form may be a bag of water soluble polymer sheet, a water soluble polymer container such as bottle, or the like.

Water soluble polymer sheet is in the market, and Solblon KA#40, Solblon KA#50, Solblon KB#40, Solblon KC#35, Solblon KC#40, Solblon KC#50, Solblon KD#40 (polyvinyl alcohol film produced by Aicello Chemical), Hi-scelon S-400AX, Hi-scelon C-200AX, Hi-scelon C-200AP (polyvinyl alcohol film produced by Nichigo film, now Nippon Synthetic Chemical Industry) Tosslon ET20 (polyvinyl alcohol film produced by Tokyo Cellophane Paper, now Tochello), Vinylon Film H4000, Vinylon Film HH4000, Vinylon Film HP4000 (polyvinyl alcohol film produced by Kuraray), Flexine (polyethylene glycol film produced by Dai-ichi Kogyo Seiyaku) and so on are available.

As the envelope substance for the enveloped pesticidal formulation of the present invention should be water soluble, it is preferable to preserve the enveloped pesticidal formulation of the present invention wrapped up in a water insoluble material for preventing the formulation from breaking by water prior to use. Examples of the water insoluble material include resins such as polyethylene, polypropylene, polystyrene, polyester, polyamide, cellophane, polyvinyl chloride, polyvinylidene chloride, acrylonitrile-butadiene-styrene, polyacrylonitrile-styrene, polyvinylidene fluoride, polytetrafluoroethylene, polycarbonate, polyacetal and so on; aluminum; and paper. These materials may be formed to bags or containers. Especially, preferred are damp-proofing processed aluminum bags which can be manufactured by pasted polyethylene or polypropylene for heat-sealing inside the aluminum sheet, and/or pasted paper, cellophane, polyester or polyamide for wrapping outside the aluminum sheet.

The enveloped pesticidal formulation of the present invention is applied after diluted with water at a suitable rate as well as ordinary solid pesticidal formulations such as wettable powders, water dispersible granules, water soluble formulations and so on. Further, the enveloped pesticidal formulation of the present invention can be applied to paddy field without diluted.

EXAMPLES

The present invention is explained in detail below, but the present invention is not limited to the following examples.

Example 1

Twenty (20) parts by weight of procymidone (fungicidally active compound), 4 parts by weight of Sorpol 5029-o (surfactant produced by Toho Chemical), 2 parts by weight of Demol SNB (surfactant produced by Kao), 60 parts by weight of Carplex CS-7 (white carbon produced by Shionogi & Co.), 10 parts by weight of glycerin and 4 parts by weight of Shokozan SP Clay (clay produced by Shokozan Kogyosho) were well mixed by a juice mixer and pulverized by a centrifugal mill to give wettable powders. Ten grams (10.0 g) of the wettable powders obtained above were enveloped in length 90 mm×width 70 mm of Solblon KC#30 (film comprising mainly polyvinyl alcohol, manufactured by Aicello Chemical). The obtained enveloped pesticidal formulation was wrapped up in a processed aluminum bag (length 100 mm×width 80 mm, polypropylene/polyethylene/aluminum/polyethylene structure) and heat-sealed.

Example 2

The same procedures were performed as Example 1, except that 5 parts by weight of ethylene glycol were used in place of 10 parts by weight of glycerin and that the used amount of Shokozan SP Clay was 9 parts by weight, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed.

Reference Example 1

The same procedures were performed as Example 1, except that glycerin was not used and that the used amount of Shokozan SP Clay was 14 parts by weight, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed.

Test Example 1

(1) The enveloped pesticidal formulations in the processed aluminum bag given in Examples 1, 2 and Reference Example 1 were kept in 60° C. for one week. Appearance of the water soluble film was observed compared with the former. The results were shown in Table 1.

(2) Each of the above formulations kept in 60° C. for one week was supplied to a solubility test.

Solubility Test

In a 1-liter beaker, 800 mL of water and a piece of magnetic stir bar were put and kept at 20° C. of the water temperature. The water was stirred with a magnetic stirrer and the rotatory number was adjusted in order to set the bottom end of the whirlpool on the 600 mL line of the beaker. The tested film was cut in a suitable size and clipped with a slide mount, which was hung in water at right angles to the current. After the film was swollen and broken, the slide mount was shaken well in the water and the residual film was thrown off. The time from the hanging the slide mount to the disappearance of the film dispersed in water was measured as the dissolving time. The results are given in Table 1.

TABLE 1

| Test No. | Tested Formulation | Water Soluble Hydroxy Compound (Parts by Weight) | Appearance of the Film (Compared with the Former) | Dissolving Time (seconds) |
| --- | --- | --- | --- | --- |
| 1-1 | Example 1 | glycerin (10) | No Changed | 37 |
| 1-2 | Example 2 | ethylene glycol (5) | No Changed | 54 |
| 1-3 | Reference Example 1 | None (0) | Hardened | 111 |

Example 3

Twenty (20) parts by weight of procymidone, 4 parts by weight of Sorpol 5029-o, 2 parts by weight of Demol SNB, 40 parts by weight of Carplex CS-7, 10 parts by weight of isobutyl alcohol and 24 parts by weight of Shokozan SP Clay were well mixed by a juice mixer and pulverized by a centrifugal mill to give wettable powders. Ten grams (10.0 g) of the wettable powders obtained above were enveloped in length 90 mm×width 70 mm of Solblon KC#30 and heat-sealed. The obtained enveloped pesticidal formulation was wrapped up in a processed aluminum bag (length 100 mm×width 80 mm, polypropylene/polyethylene/aluminum/polyethylene structure) and heat-sealed.

Example 4

The same procedures were performed as Example 3, except that ethylene glycol monomethyl ether acetate was used in place of isobutyl alcohol, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed.

Reference Example 2

The same procedures were performed as Example 3, except that isobutyl alcohol was not used and that the used amount of Shokozan SP Clay was 34 parts by weight, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed.

Test Example 2

The preservation test and the solubility test were performed in the same manner as Test Example 1 using the enveloped pesticidal formulations in the processed aluminum bag obtained Example 3, 4 and Reference Example 2. The results are given in Table 2.

TABLE 2

| Test No. | Tested Formulation | Water Soluble Hydroxy Compound (Parts by Weight) | Appearance of the Film (Compared with the Former) | Dissolving Time (seconds) |
|---|---|---|---|---|
| 2-1 | Example 3 | isobutyl alcohol (10) | No Changed | 64 |
| 2-2 | Example 4 | EGMEAC* (10) | No Changed | 67 |
| 2-3 | Reference Example 2 | None (0) | Hardened | 77 |

*EGMEAC; ethylene glycol monomethyl ether acetate

Example 5

Twenty (20) parts by weight of tolclofos-methyl (fungicidally active compound), 4 parts by weight of Sorpol 5029-o, 2 parts by weight of Demol SNB, 40 parts by weight of Carplex CS-7, 10 parts by weight of glycerin and 24 parts by weight of Shokozan SP Clay were well mixed by a juice mixer and pulverized by a centrifugal mill to give wettable powders. Ten grams (10.0 g) of the wettable powders obtained above were enveloped in length 90 mm×width 70 mm of Solblon KC#30. The obtained enveloped pesticidal formulation was wrapped up in a processed aluminum bag (length 100 mm×width 80 mm, polypropylene/polyethylene/aluminum/polyethylene structure) and heat-sealed.

Example 6

The same procedures were performed as Example 5, except that 5 parts by weight of ethylene glycol was used in place of 10 parts by weight of glycerin and that the used amount of Shokozan SP Clay was 29 parts by weight, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed in the same manner as Example 3.

Reference Example 3

The same procedures were performed as Example 1, except that glycerin was not used and that the used amount of Shokozan SP Clay was 34 parts by weight, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed in the same manner as Example 4.

Test Example 3

The preservation test and the solubility test were performed in the same manner as Test Example 1 using the enveloped pesticidal formulations in the processed aluminum bag obtained Example 5, 6 and Reference Example 3. The results are given in Table 3.

TABLE 3

| Test No. | Tested Formulation | Water Soluble Hydroxy Compound (Parts by Weight) | Appearance of the Film (Compared with the Former) | Dissolving Time (seconds) |
|---|---|---|---|---|
| 3-1 | Example 5 | glycerin (10) | No Changed | 37 |
| 3-2 | Example 6 | ethylene glycol (5) | No Changed | 37 |
| 3-3 | Reference Example 3 | None (0) | Hardened | 153 |

Example 7

Twenty (20) parts by weight of flumiclorac-pentyl (herbicidally active compound), 4 parts by weight of Sorpol 5029-o, 2 parts by weight of Demol SNB, 20 parts by weight of Carplex CS-7, 10 parts by weight of glycerin and 44 parts by weight of Shokozan SP Clay were well mixed by a juice mixer and pulverized by a centrifugal mill to give wettable powders. Ten grams (10.0 g) of the wettable powders obtained above were enveloped in length 90 mm×width 70 mm of Solblon KC#30. The obtained enveloped pesticidal formulation was wrapped up in a processed aluminum bag (length 100 mm×width 80 mm, polypropylene/polyethylene/aluminum/polyethylene structure) and heat-sealed.

Example 8

The same procedures were performed as Example 7, except that 5 parts by weight of ethylene glycol was used in place of 10 parts by weight of glycerin and that the used amount of Shokozan SP Clay was 49 parts by weight, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed in the same manner as Example 6.

Reference Example 4

The same procedures were performed as Example 6, except that glycerin was not used and that the used amount of Shokozan SP Clay was 34 parts by weight, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed in the same manner as Example 7.

Test Example 4

The preservation test and the solubility test were performed in the same manner as Test Example 1 using the enveloped pesticidal formulations in the processed aluminum bag obtained Example 7, 8 and Reference Example 4. The results are given in Table 4.

TABLE 4

| Test No. | Tested Formulation | Water Soluble Hydroxy Compound (Parts by Weight) | Appearance of the Film (Compared with the Former) | Dissolving Time (seconds) |
| --- | --- | --- | --- | --- |
| 4-1 | Example 7 | glycerin (10) | No Changed | 42 |
| 4-2 | Example 8 | ethylene glycol (5) | No Changed 29 | |
| 4-3 | Reference Example 4 | None (0) | Hardened | 94 |

Example 9

Eighteen (18) parts by weight of permethrin (insecticidally active compound), 4 parts by weight of Sorpol 2495G (surfactant produced by Toho Chemical), 18 parts by weight of Demol SNB, 0.9 part by weight of Serogen 7A (sodium carboxymethylcellulose produced by Dai-ichi Kogyo Seiyaku), 6 parts by weight of Carplex CS-7, 4 parts by weight of glycerin and 51.3 parts by weight of Radiolight #200 (calcined silica produced by Showa Kagaku Kogyo) were well mixed by a juice mixer and pulverized by a centrifugal mill to give wettable powders. Ten grams (10.0 g) of the wettable powders obtained above were enveloped in length 90 mm×width 70 mm of Solblon KC#30. The obtained enveloped pesticidal formulation was wrapped up in a processed aluminum bag (length 100 mm×width 80 mm, polypropylene/polyethylene/aluminum/polyethylene structure) and heat-sealed.

Reference Example 5

The same procedures were performed as Example 9, except that glycerin was not used and that 10 parts by weight of Shokozan SP Clay was used, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed in the same manner as Example 8.

Test Example 5

The preservation test and the solubility test were performed in the same manner as Test Example 1 using the enveloped pesticidal formulations in the processed aluminum bag obtained Example 9 and Reference Example 5. The results are given in Table 5.

TABLE 5

| Test No. | Tested Formulation | Water Soluble Hydroxy Compound (Parts by Weight) | Appearance of the Film (Compared with the Former) | Dissolving Time (seconds) |
| --- | --- | --- | --- | --- |
| 5-1 | Example 9 | glycerin (4) | No Changed | 67 |
| 5-2 | Reference Example 5 | None (0) | Hardened | 79 |

Example 10

Forty-five (45) parts by weight of flumioxazine, 1.35 parts by weight of Morwet EFT (surfactant produced by Wittoco), 9 parts by weight of Morwet D425 (surfactant produced by Wittoco), 10 parts by weight of glycerin and 34.65 parts by weight of ASP 400P (aluminium silicate produced by Engelhard) were well mixed by a juice mixer and pulverized by a centrifugal mill to give wettable powders. Ten grams (10.0 g) of the wettable powders obtained above were enveloped in length 90 mm×width 70 mm of Solblon KC#30. The obtained enveloped pesticidal formulation was wrapped up in a processed aluminum bag (length 100 mm×width 80 mm, polypropylene/polyethylene/aluminum/polyethylene structure) and heat-sealed.

Reference Example 6

The same procedures were performed as Example 9, except that Carplex CS-7 was used in place of glycerin, to give an enveloped pesticidal formulation. Then, the obtained enveloped pesticidal formulation was wrapped up in a processed aluminum bag (length 100 mm×width 80 mm, polypropylene/polyethylene/aluminum/polyethylene structure) and heat-sealed in the same manner as Example 9.

Test Example 6

The preservation test and the solubility test were performed in the same manner as Test Example 1 using the enveloped pesticidal formulations in the processed aluminum bag obtained Example 10 and Reference Example 6. The results are given in Table 6.

TABLE 6

| Test No. | Tested Formulation | Water Soluble Hydroxy Compound (Parts by Weight) | Appearance of the Film (Compared with the Former) | Dissolving Time (seconds) |
| --- | --- | --- | --- | --- |
| 6-1 | Example 10 | glycerin (10) | No Changed | 47 |
| 6-2 | Reference Example 6 | None (0) | Hardened | 74 |

What is claimed is:

1. A solid pesticidal formulation enveloped in a water soluble substance wherein the solid pesticidal formulation comprises glycerin and the solid pesticidal formulation is a formulation selected from wettable powders, water dispersible granules and water soluble formulations.

2. The enveloped pesticidal formulation according to claim 1, wherein the content of glycerin is 0.1 to 40% by weight, based on the weight of the solid formulation.

3. The enveloped pesticidal formulation according to claim 1, wherein the content of glycerin is 2 to 20% by weight, based on the weight of the solid formulation.

\* \* \* \* \*